(12) United States Patent
Manuel et al.

(10) Patent No.: US 11,053,572 B2
(45) Date of Patent: Jul. 6, 2021

(54) BIODEGRADABLE MAGNESIUM ALLOYS, METHODS OF MANUFACTURE THEREOF AND ARTICLES COMPRISING THE SAME

(71) Applicant: University of Florida Research Foundation, Inc., Gainesville, FL (US)

(72) Inventors: Michele Manuel, Gainesville, FL (US); Josephine Allen, Gainesville, FL (US); Jordan P. Ball, Gainesville, FL (US); Harpreet Singh Brar, Hillsboro, OR (US); Ida Svensson Berglund, Evanston, IL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 404 days.

(21) Appl. No.: 16/277,173

(22) Filed: Feb. 15, 2019

(65) Prior Publication Data
US 2019/0194782 A1    Jun. 27, 2019

Related U.S. Application Data

(62) Division of application No. 14/901,409, filed as application No. PCT/US2014/045364 on Jul. 3, 2014, now Pat. No. 10,266,922.
(Continued)

(51) Int. Cl.
*C23C 8/10* (2006.01)
*C22C 23/00* (2006.01)
(Continued)

(52) U.S. Cl.
CPC ............ *C22C 23/00* (2013.01); *A61L 27/047* (2013.01); *A61L 27/306* (2013.01); *A61L 27/58* (2013.01);
(Continued)

(58) Field of Classification Search
CPC ....... C22C 23/00; C22C 23/06; A31L 27/047; A31L 27/306; A31L 27/58; C22F 1/06
See application file for complete search history.

(56) References Cited

U.S. PATENT DOCUMENTS

| 4,713,004 A | 12/1987 | Linkow |
| 4,791,929 A | 12/1988 | Jarrett |

(Continued)

FOREIGN PATENT DOCUMENTS

| EP | 2014319 A1 | 1/2009 |
| EP | 2022443 B1 | 2/2009 |
| WO | WO2011105685 A2 | 9/2011 |

OTHER PUBLICATIONS

Brar H.P. Dissertation. University of Florida, Apr. 23, 2012, pp. 139.
(Continued)

*Primary Examiner* — Lois L Zheng
(74) *Attorney, Agent, or Firm* — Thomas|Horstemeyer, LLP

(57) ABSTRACT

Disclosed herein is an article comprising a metal alloy; where the metal alloy comprises a base metal, a second element and a third element; where the base metal is magnesium, calcium, strontium, zinc, or a combination thereof; where the second element is chemically different from the third element; and where the second element and the third element are scandium, yttrium, gadolium, cerium, neodymium, dysporium, or a combination thereof; and a protective layer disposed upon the metal alloy and is reactively bonded to the metal alloy; where the protective layer comprises a base non-metallic derivative, a second non-metallic derivative and a third non-metallic derivative of metals present in the metal alloy; and where the base non-metallic derivative, the second non-metallic derivative and the third non-metallic derivative are all chemically different from one another.

20 Claims, 10 Drawing Sheets

Related U.S. Application Data

(60) Provisional application No. 61/842,456, filed on Jul. 3, 2013.

(51) Int. Cl.

| | | |
|---|---|---|
| *C22C 23/06* | (2006.01) | |
| *A61L 27/04* | (2006.01) | |
| *A61L 27/30* | (2006.01) | |
| *A61L 27/58* | (2006.01) | |
| *C22C 1/04* | (2006.01) | |
| *C22F 1/06* | (2006.01) | |

(52) U.S. Cl.
CPC ............ *C22C 1/0408* (2013.01); *C22C 23/06* (2013.01); *C22F 1/06* (2013.01); *A61L 2400/18* (2013.01); *A61L 2420/02* (2013.01)

(56) References Cited

U.S. PATENT DOCUMENTS

| | | |
|---|---|---|
| 6,896,517 B1 | 5/2005 | Bjoern |
| 7,771,774 B2 | 8/2010 | Berckmans, III |
| 8,197,480 B2 | 6/2012 | Roller et al. |
| 8,968,002 B2 | 3/2015 | Purga |
| 2003/0087197 A1 | 5/2003 | Schulman |
| 2004/0241314 A1 | 12/2004 | Li |
| 2005/0079200 A1 | 4/2005 | Rathenow |
| 2005/0250073 A1 | 11/2005 | Tresser |
| 2005/0266041 A1 | 12/2005 | Gerold et al. |
| 2006/0198869 A1 | 9/2006 | Furst et al. |
| 2008/0118893 A1 | 5/2008 | Armellini |
| 2008/0243242 A1 | 10/2008 | Kappelt |
| 2008/0312736 A1 | 12/2008 | Mueller |
| 2009/0131540 A1 | 5/2009 | Hiromoto |
| 2009/0226857 A1 | 9/2009 | Grant |
| 2010/0075162 A1 | 3/2010 | Yang et al. |
| 2010/0106243 A1 | 4/2010 | Wittchow |
| 2010/0161031 A1 | 6/2010 | Papirov et al. |
| 2011/0054629 A1 | 3/2011 | Seok et al. |
| 2011/0076319 A1 | 3/2011 | Orlowski et al. |
| 2011/0319986 A1 | 12/2011 | Bayer |
| 2014/0154341 A1 | 6/2014 | Manuel |

OTHER PUBLICATIONS

Staiger et. al. Biomaterials, 27, 2006, 1728.
Ott et. al. Corrosion Science, 75, 2013, 201.
Gunde et. al. Material Science Forum, vols. 618-619, 2009, 71.
Berglund, Ida S . . . et al.; "Synthesis and Characterization of Mg—Ca—Sr Alloys for Biodegradable Orthopedic Implant Applications"; Society for Biomaterials; 06i12/2012; pp. 1524-1534.
Bornapour, M., et al.; "Biocompabbility and Biodegradability of Mg—Sr Alloys: The Formation of Sr-Substituted Hydroxyapatite"; Acta Biomaterialia vol. 9 (2013); Aug. 5, 2012: pp. 5319-5330.
Brar, H. S. et al. "A study of biodegradable Mg—3Sc—3Y alloy and the effect of surface passivation on in-vitro degradation" Acta Biomaterialia 9 (2013) 5331-5340.
Brar, Harpreet; Wong, Joey; Manuel, Michele; "Investigation of the mechanical and degradation properties of Mg—Sr and Mg—Zn—Sr alloys for use as potential biodegradable implant materials." Source: Journal of the Mectmical Behavior of Biomedical Material.
Oien SL, Daniei S, Zhang F, Chang YA, Yan XY, Xie FY, Schmid-Fetzer R, Oates WA "The PANDAT Software Package and its Applications" CALPHAD 2002; 26: (175-188).
International Preliminary Report on Patentability for Application No. PCTiUS2011 /042892 Filing Date Jul. 2, 2011; dated Jan. 8, 2013 (6 pages).
International Search Report for Application No. PCT/US2011/042892 Filing Date Jul. 2, 2011; dated Mar. 20, 2012 (4 pages).
International Search Report for Application No. PCT/US2014/045364 Filing Date Jul. 3, 2014; dated Oct. 28, 2014 (6 pages).
International Search Report for Application No. PCT/US2014/064065 Filing Date Nov. 5, 2014; dated Feb. 18, 2015 (8 pages).
Li Z, Gu X, Lou S, Zheng Y. "The development of binary Mg—Ca alloys for use as biodegradable materials within bone" Biomaterials 2007; 29: (1329-1344).
Wan Y, Xiong G, Luo H, He F, Huang Y, Zhou X. "Preparation and characterization of a new biomedical magnesium-calcium alloy" Materials & Design 2008; 29: (2034-2037).
Written Opinion for Application No. PCT/US2011 /042892 Filing Date Jul. 2, 2011; dated Mar. 20, 2012 (5 pages).
Written Opinion for Application No. PCT/US2014/064065 Filing Date Nov. 5, 2014; dated Feb. 18, 2015 (5 pages).
Written Opinion for International Application No. PCT/US2014/045364 Filing Date Jul. 3, 2014; dated Oct. 28, 2014 (9 pages).

BIODEGRADABLE MAGNESIUM ALLOYS, METHODS OF MANUFACTURE THEREOF AND ARTICLES COMPRISING THE SAME

CROSS-REFERENCE TO RELATED APPLICATIONS

This application is a divisional application of co-pending U.S. patent application Ser. No. 14/901,409, filed on Dec. 28, 2015, entitled "BIODEGRADABLE MAGNESIUM ALLOYS, METHODS OF MANUFACTURE THEREOF AND ARTICLES COMPRISING THE SAME," which is a 35 U.S.C. § 371 national stage application of PCT Application No. PCT/US14/045364 filed on Jul. 3, 2014, which claims priority to and the benefit of U.S. Provisional Patent Application No. 61/842,456 filed on Jul. 3, 2013, each of which is hereby incorporated by reference in its entirety.

BACKGROUND

This disclosure relates to biodegradable magnesium alloys, methods of manufacture thereof and articles comprising the same.

Magnesium and its alloys have been investigated for use as materials in biodegradable implants. Although properties of magnesium such as biocompatibility and susceptibility to dissolution are desirable for biodegradable implant applications, its high degradation rate and low strength pose a significant challenge in applications where a longer life cycle (in the body of a living being) is desired.

Elements like aluminum, zinc, calcium, rare earth and other elements have been alloyed with magnesium to improve the mechanical properties of magnesium and to reduce the degradation rate of magnesium and its alloys. In addition to alloying, organic and conversion coatings like micro arc oxidation (MAO) and calcium phosphate coatings have also been employed to develop magnesium-based materials with low degradation rates. These coatings have shown promising results, leading to approximately 70 to 80% initial reduction in degradation rate with calcium phosphate coatings and almost 90% reduction with MAO as compared to uncoated samples. Although these techniques show an improved degradation behavior, they often require specialized equipment, surface pre-treatments and/or simplified substrate geometries. For example, coating a porous metallic foam implant would be difficult using these technologies.

It is therefore desirable find methods and compositions to control the degradation rate of magnesium and its alloys, when these alloys are used in the body of living beings.

SUMMARY

Disclosed herein is an article comprising a metal alloy; where the metal alloy comprises a base metal, a second element and a third element; where the base metal is magnesium, calcium, strontium, zinc, or a combination thereof; where the second element is chemically different from the third element; and where the second element and the third element are scandium, yttrium, gadolium, cerium, neodymium, dysporium, or a combination thereof; and a protective layer disposed upon the metal alloy and is reactively bonded to the metal alloy; where the protective layer comprises a base non-metallic derivative, a second non-metallic derivative and a third non-metallic derivative of metals present in the metal alloy; and where the base non-metallic derivative, the second non-metallic derivative and the third non-metallic derivative are all chemically different from one another.

Disclosed herein too is a method comprising blending three or more metals to form a metal alloy; molding the metal alloy; and annealing the metal alloy at a temperature and in an atmosphere effective to produce a protective layer on the metal alloy; where the protective layer is reactively bonded to the metal alloy and where the protective layer is non-metallic.

Disclosed herein too is a method comprising disposing in the body of a living being an article comprising a metal alloy; where the metal alloy comprises a base metal, a second element and a third element; where the base metal is magnesium, calcium, strontium, or a combination thereof; where the second element is chemically different from the third element; and where the second element and the third element are scandium, yttrium, gadolium, cerium, neodymium, dysporium, or a combination thereof; and a protective layer disposed upon the metal alloy and is reactively bonded to the metal alloy; where the protective layer comprises a base non-metallic derivative, a second non-metallic derivative and a third non-metallic derivative of metals present in the metal alloy; and where the base non-metallic derivative, the second non-metallic derivative and the third non-metallic derivative are all chemically different from one another.

DETAILED DESCRIPTION

Figure 1:
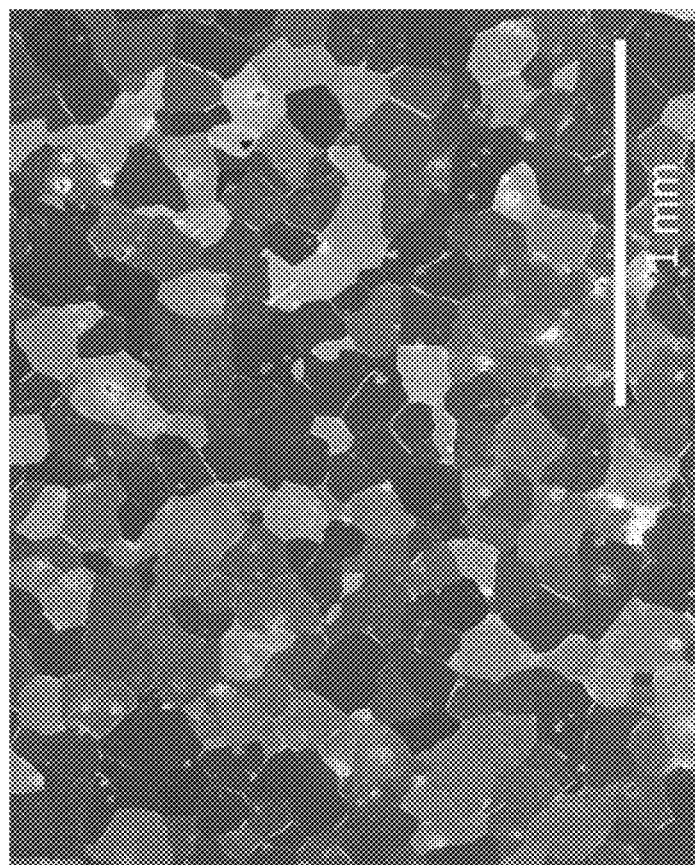
FIG. 1 is a an optical image showing the microstructure of solution treated Mg-3Sc-3Y alloy; it depicts fine equiaxed grains with an average size of 109 μm.

Disclosed herein are articles (e.g., biodegradable implants) that comprise a metal alloy that comprises three or more elements and that have disposed upon the article a non-toxic protective layer that facilitates control of the degradation characteristics of the article when it is disposed inside the body of a living being. In one embodiment, the protective layer comprises an oxide, a carbide, an oxycarbide, a nitride, an oxynitride, a boride, a borocarbide, a boronitride, a silicide, an iodide, a bromide, a sulfide, a selenide, a telluride, a fluoride, or a borosilicide of the metal alloy. The protective layer can also comprise two or more oxides, carbides, oxycarbides, nitrides, oxynitrides, borides, borocarbides, boronitrides, silicides, iodides, bromides, sulfides, selenides, tellurides, fluorides or borosilicides of the metal alloy. The protective layer can also comprise a mixture of two or more of the following: an oxide, a carbide, a oxynitride, a nitride, a oxynitride, a boride, a borocarbide, a boronitride, a silicide, an iodide, a bromide, a sulfide, a selenide, a telluride, a fluoride or a borosilicide of the metal alloy.

The protective layer reduces the rate of degradation of the biodegradable implant when it is disposed inside the body of a living being. The rate of degradation can be tailored depending upon the composition and thickness of the protective layer. The use of the protective layer provides a plurality of stages in the degradation of the metal alloys. In an exemplary embodiment, the use of the protective layer provides a 2-stage degradation process for articles that are manufactured from the metal alloys. The protective layer is advantageous in that it reduces the initial rate of degradation by up to 90% when compared with an article that does not have the protective coating.

As noted above, the metal alloy comprises 3 or more elements (i.e., it is a ternary alloy). In one embodiment, the metal alloy comprises 4 or more elements. In another embodiment, the metal alloy comprises 5 or more elements. In an exemplary embodiment, the metal alloy comprises of 3 or more elements. The metal alloy comprises a base metal, a second element and a third element. The metal alloy has the formula (1) shown below:

$$M_xM_yM_z \quad (1)$$

where $M_x$ is a base metal, $M_y$ is a second element and $M_z$ is a third element, where x, y and z represent the weight fractions of the respective metals in the metal alloy and where the sum of x, y and z is equal to 100% (if measured in terms of a percentage) or 1 (if measured in terms of a fraction). For example, if the base metal constitutes 70 weight percent (wt %) of the metal alloy, the second element constitutes 20 wt % of the metal alloy and the third element constitutes 10 wt % of the metal alloy, then x=0.7, y=0.2 and z=0.1 and the sum of x, y and z=1 or x=70%, y=20% and z=10% and the sum of x, y and z=100%. It is to be noted that the second and the third elements are metals.

The base metal is that metal that is present in the metal alloy in the largest amount. The base metal comprises magnesium, calcium, strontium, zinc or a combination comprising at least one of the foregoing base metals. The base metal is present in the metal alloy in an amount of about 40 to about 99 wt %, specifically about 50 to 98 wt %, and more specifically about 60 to about 97 wt %, based on the total weight of the metal alloy. An exemplary base metal is magnesium.

The second element and the third element are different in composition from each other and are selected from the group consisting of scandium, yttrium, gadolinium, cerium neodymium, dysprosium, or a combination thereof.

The second element is present in an amount of about 0.5 to about 40 wt %, specifically about 0.5 to 20 wt %, and more specifically about 1.0 to about 5 wt %, based on the total weight of the metal alloy. In an exemplary embodiment, the second element is scandium.

The third element is present in an amount of about 0.1 to about 20 wt %, specifically about 1 to about 8 wt %, and more specifically about 1.5 to about 4 wt %, based on the total weight of the metal alloy. In an exemplary embodiment, the third element is yttrium.

The weight ratio of the second element to the third element is about 0.2:1 to about 1:0.25, specifically about 0.5:1 to about 1:0.5, and more specifically about 0.75:1 to 1:0.75.

Minor amounts of other elements may be added to the metal alloy to refine the structure. Examples of such elements are manganese and zirconium. These elements are added in amounts of 0.1 to about 1 wt %, based on the total weight of the alloy.

In one embodiment, when magnesium is used as the base metal, scandium is used as the second element and yttrium is used as the third element. The magnesium is used in amounts of about 92 to about 96 wt %, while scandium is used in amounts of about 1.5 to about 4.0 wt %, while yttrium is used in amounts of about 1.5 to about 4.0 wt %.

The protective layer reduces the rate of degradation of the metal alloy thus assuring that the resorbable implant can be used in the body of a living being, but for an extended period of time when compared with a resorbable implant that does not have the protective coating. In short, it increases the life of the implant, when disposed inside the body. By slowing down the initial rate of degradation, the implant lasts a longer time when it is disposed inside the body of a living being. The degradation products of the metal alloy and the protective layer both show no toxicity to osteoblastic cells and cell proliferation studies have shown cell attachment and cell proliferation on the surface of the oxidized alloy.

The protective layer is reactively bonded (i.e., it is covalently bonded or ionically bonded) to the metal alloy. The protective layer does not contain metals, but comprises non-metallic derivatives of the elements contained in the metal alloy. The non-metallic derivatives are an oxide, a carbide, an oxycarbide, a nitride, an oxynitride, a boride, a borocarbide, a boronitride, a silicide, an iodide, a bromide, a sulfide, a selenide, a telluride, a fluoride, a borosilicide of the elements of the metal alloy, or a combination thereof. The protective layer is grown from at least one of the components of the metal alloy and is disposed upon the metal alloy and is in direct contact with the metal alloy. The protective layer may comprise a plurality of layers. In one embodiment, the protective layer comprises one or more layers. In another embodiment, the protective layer comprises two or more layers. In an exemplary embodiment, the protective layer comprises one or more layers. If the protective layer comprises two or more layers, then each layer will have a different chemistry.

Each protective layer comprises one or more non-metallic derivatives. The non-metallic derivatives may comprise a base non-metallic derivative, an optional second non-metallic derivative and an optional third non-metallic derivative of the respective metals that are present in the metal alloy.

Each protective layer comprises about 1 to about 100 wt %, specifically about 5 to about 95 wt %, and more specifically about 10 to about 90 wt % of a base non-metallic derivative layer, based on the total weight of the protective layer. The protective layer can also optionally comprises a second non-metallic derivative and a third non-metallic derivative. The second non-metallic derivative is present in an amount of about 0.5 to about 50 wt %, specifically about 1 to about 45 wt %, based on the total weight of the protective layer. The third non-metallic derivative is present in an amount of about 0.5 to about 50 wt %, specifically about 1 to about 45 wt %, based on the total weight of the protective layer. The second and the third non-metallic derivative are not chemically identical with one another.

In an exemplary embodiment, the base non-metallic derivative comprises an oxide, a carbide, an oxycarbide, a nitride, an oxynitride, a boride, a borocarbide, a boronitride, a silicide, an iodide, a bromide, a sulfide, a selenide, a telluride, a fluoride, or a borosilicate of magnesium, calcium, strontium, zinc or a combination comprising at least one of the foregoing metals. In another exemplary embodiment, the second non-metallic derivative and the third non-metallic derivative comprise an oxide, a carbide, an oxycarbide, a nitride, an oxynitride, a boride, a borocarbide, a boronitride, a silicide, an iodide, a bromide, a sulfide, a selenide, a telluride, a fluoride, or a borosilicide of scandium, yttrium, gadolinium, cerium neodymium, dysprosium, or a combination thereof.

In one embodiment, the non-metallic derivatives in a given protective layer may all be oxides, carbides, or the like, of the metals used in the metal alloys. In another embodiment, some of non-metallic derivatives in a given protective layer may be oxides, while other non-metallic derivatives in the same protective layer may be carbides, borides, or the like, of the metals used in the metal alloys. For example, the base non-metallic derivative, the second non-metallic derivative and the third non-metallic derivative can all be oxides, or all be carbides of the metals in the metal alloy. In another example, the base non-metallic derivative and the second non-metallic derivative may be an oxide of one of the metals in the metal alloy, while the third non-metallic derivative may be a carbide, or a boride, of the metals in the metal alloy.

In an exemplary embodiment, when the metal alloy comprises magnesium, scandium, yttrium, or zinc, the base non-metallic derivative comprises magnesium oxide, while the second non-metallic derivative comprises scandium oxide and the third non-metallic derivative comprises yttrium oxide. The protective layer thus comprises magnesium oxide, scandium oxide and yttrium oxide.

In another exemplary embodiment, when the metal alloy comprises magnesium, scandium and yttrium, the base non-metallic derivative comprises magnesium carbide, while the second non-metallic derivative comprises scandium carbide and the third non-metallic derivative comprises yttrium carbide. The protective layer thus comprises magnesium carbide, scandium carbide and yttrium carbide.

In yet another exemplary embodiment, when the metal alloy comprises magnesium, scandium and yttrium, the base non-metallic derivative comprises magnesium nitride, while the second non-metallic derivative comprises scandium nitride and the third non-metallic derivative comprises yttrium nitride. The protective layer thus comprises magnesium nitride, scandium nitride and yttrium nitride.

In yet another exemplary embodiment, when the metal alloy comprises magnesium, scandium and yttrium, the base non-metallic derivative comprises magnesium boride, while the second non-metallic derivative comprises scandium boride and the third non-metallic derivative comprises yttrium boride. The protective layer thus comprises magnesium boride, scandium boride and yttrium boride.

In another exemplary embodiment, the protective layer may comprise a single layer that comprises a magnesium oxide, yttrium carbide and scandium carbide. In another embodiment, the protective layer may comprise plurality of layers, where the outermost protective layer comprises a large amount of magnesium oxide, while the inner protective layer comprises a large amount scandium oxide and yttrium oxide. In one embodiment, the protective layer comprises a first layer that comprises a larger amount of a first metal oxide than the second metal oxide or the third metal oxide. In one embodiment, the first layer of the protective layer comprises a larger amount of the first metal oxide than the combined amount of the second metal oxide and the third metal oxide. The first metal oxide layer has a thickness of 1 to 200 nanometers, specifically 5 to 80 nanometers, and more specifically 10 to 50 nanometers.

The protective layer also comprises a second layer that comprises a larger amount of the second metal oxide or the third metal oxide when compared with the amount of the first metal oxide. In one embodiment, the protective layer also comprises a second layer that comprises a larger combined amount of the second metal oxide and third metal oxide when compared with the amount of the first metal oxide. The second metal oxide layer is generally in direct contact with the first metal oxide layer and has a thickness of 1 to 300 nanometers, specifically 5 to 175 nanometers, and more specifically 10 to 150 nanometers. The protective layer thus has a thickness of 1 to 500 nanometers, specifically 5 to 275 nanometers, and more specifically 10 to 250 nanometers.

In another exemplary embodiment, the protective layer may comprises two layers—a first layer that comprises an oxide, a carbide, an oxycarbide, a nitride, an oxynitride, a boride, a borocarbide, a boronitride, a silicide, an iodide, a bromide, a sulfide, a selenide, a telluride, a fluoride, a borosilicide of the metals present in the metal alloy, while the second layer comprises a different composition than that of the first layer. The second layer may be an oxide, a carbide, an oxycarbide, a nitride, an oxynitride, a boride, a borocarbide, a boronitride, a silicide, an iodide, a bromide, a sulfide, a selenide, a telluride, a fluoride, or a borosilicide of the metal present in the metal alloy, and is different from the first layer.

In one embodiment, in one method of manufacturing an article, the metals used in the metal alloy are first blended together, melted and molded to form the desired article. The metals may be in pure form or may be in the form of alloys, which are then blended together. The article comprising the metal alloy is then reacted with the desired elements in order to produce the protective layer on the article. For example, if it is desired to produce a layer of oxide on the metal alloy, the article is annealed in an atmosphere of oxygen for a desired period of time. The thickness of the protective layer may be changed by changing the time, the temperature, the pressure, or the composition of the gaseous atmosphere in which the oxidation takes place.

In one embodiment, the protective layer is produced by annealing the metal alloy at a temperature of about 100 to about 650° C., in an atmosphere that contains the desired reactants that facilitate the formation of the protective layer. For example, in order to produce a protective layer that comprises oxides, the metal alloy is annealed in an atmosphere of oxygen. If the protective layer comprises a carbide, then the metal alloy is annealed in a carbonaceous atmosphere (e.g., carbon monoxide, carbon dioxide, alkanes, alkylenes, and the like). Similarly, atmospheres comprising boron, nitrogen, silicon, and the like may be used to create protective layers that comprise borides, nitrides, silicides, or the like, or combinations thereof. The protective layer has a thickness of 1 nanometer to 500 nanometers.

The atmosphere in which the annealing is conducted may comprise an inert gas in addition to the reactive gas. For example, the atmosphere used to produce an oxide may include a combination of argon (or any other inert gas) and oxygen, while the atmosphere to produce a carbide may include a combination of argon and carbon.

In one method of using the article, the article having the desired protective layer is placed inside the body of a living being. The article may be polished prior to being inserted into the body of the living being. Since the protective layer has a different degradation rate from that of the metal alloy, the article has a longer life cycle than an article that that does not have a protective layer. The hydrogen production rate (where the hydrogen is a byproduct of decomposition of the metal alloy) is significantly reduced as a result of the use of the protective layer on the metal alloy. The article is slowly absorbed into the body without any toxic reactants being generated.

The article and the method of manufacturing and using is exemplified by the following non-limiting examples.

EXAMPLE

Example 1

Preparation of the Metal Alloy

Mg-3Sc-3Y alloy was prepared by mixing Mg-8Sc and Mg-16Y master alloys with pure magnesium. (99.98%, Sigma-Aldrich, St. Louis, Mo.). The master alloys were used for improved compositional accuracy and uniformity of the melt. The mixtures were melted in graphite crucibles at 825° C. for 1 hour, stirred once using a graphite rod and poured into a graphite mold. The ternary alloy was then prepared by mixing the master alloys with pure magnesium, melting them at 750° C. for 45 minutes and then pouring it into graphite molds. The cast alloy was allowed to air-cool to room temperature. A protective argon (Ar) atmosphere was maintained throughout the melting and casting processes to prevent any oxidation. The composition of the alloys was determined using inductively coupled plasma spectroscopy (ICP-AES, Perkin-Elmer Optima 3200 RL, Perkin Elmer, Waltham, Mass.). The ingots of Mg-3Y-3Sc were encapsulated in Pyrex tubes under an argon atmosphere and homogenized for 10 hours at 500° C., followed by a water quench.

The samples for microstructure analysis were cut from homogenized ingot and polished to a surface roughness of 0.03 μm using colloidal silica. The samples for grain size measurement were etched using acetic picral. Lineal intercept method outlined in ASTM Standard E112 was used for grain size measurements. The microstructural characterization of the samples was performed using optical microscopy (LOM, Olympus PME3; Olympus Corporation, Tokyo, Japan), scanning electron microscopy (SEM, JEOL 6335F FEG-SEM; JEOL Ltd., Tokyo, Japan) and x-ray diffraction (XRD, Philips APD 3720; Koninklijke Philips Electronics N.V., Amsterdam, The Netherlands).

Preparation of the Protective Layer

The samples for the oxidation behavior analysis were cut and polished to remove any native oxide on the surface. The polished samples were immediately placed in a tube furnace to prevent any room temperature oxidation. The samples were then heated at 500° C. in high purity oxygen and weighed after 0.5, 1, 2, 3, 4, 5, 10, 15, 20 and 25 hours. Analysis was performed on the weight gain data to determine the oxidation kinetics. The dimensions of the samples were assumed to be constant throughout the oxidation process and the dimensional changes before and after oxidation were ignored. The thickness and composition of the oxide layer were analyzed using SEM and auger electron spectroscopy (AES). Additionally, XRD and x-ray photoelectron spectroscopy (XPS) were employed to characterize the structure and chemical nature of the oxide. The operating voltage and current for AES was kept at 10 kV and 100 nA. A 3 kV Ar beam was applied for sputtering and the sputter rate was estimated to be approximately 3.75 nm/min. For XPS analysis, the instrument was operated at 15 kV and 200 mA. A monochromated Al Kα (1486.6 eV) radiation was employed as an x-ray source.

Tests and Characterization

The apparatus used for immersion tests was similar to that described in Song GL. Control of biodegradation of biocompatable magnesium alloys. Corros Sci 2007; 49:1696-701. As-polished and oxidized samples (5 hour and 24 hour oxidation) were immersed in Hanks' balanced salt solution (Thermo Scientific Inc., Waltham, Mass.) at 37° C., with a volume to surface area ratio of about 150. The hydrogen evolution of corroding specimens was measured as a function of time. The measurements were taken every 24 hours until the surface area of the specimen could no longer be calculated due of the accumulation of corrosion products. The degradation products were investigated using scanning electron microscopy (SEM) and x-ray diffraction (XRD).

Vickers microhardness testing and compression testing was employed to investigate the hardness and compressive strength of the alloy. A force of 300 gf was applied for 15 seconds for microhardness testing. Compression testing was conducted using a universal testing machine (Instron 5582; ITW, Glenview, Ill.) at a strain rate of 6% $min^{-1}$. The 0.2% offset method was used to calculate the yield strength of the samples.

Oxidized alloy samples were sterilized in ethanol one hour prior to cell seeding. 7F2 mouse osteoblasts (ATCC, Manassas, Va.) were seeded at a density of 6000 cells/$cm^2$ directly onto alloy samples in Minimum Essential Medium (MEM)-α containing 2 mM 1-glutamine, 1 mM sodium pyruvate, and 10% v/v fetal bovine serum (Invitrogen, Grand Island, N.Y.). Cell cultures were maintained in humidified environment with 5% $CO_2$ at 37° C. for 6 days. Culture medium was collected after two, four, and six days and assayed for lactate dehydrogenase (LDH), an indicator of the loss of cell membrane integrity, and thus cytotoxicity. LDH in media extracts was quantified using a multiwell assay kit (Cyto Tox-ONE, Promega, Madison, Wis.). LDH levels were then normalized to DNA content that was quantified via Picogreen DNA assay kit (Invitrogen, Grand Island, N.Y.). A high toxicity control, representing total cell lysis, was achieved by incubating cells cultured on TCPS in complete media supplemented with Triton X-100 to a final concentration of 1% for 45 minutes. Cells cultured without Triton X-100 in complete growth media served as a low toxicity control.

Toxicity of Degradation Products

Unoxidized alloy samples were incubated in 1 ml MEM-α per $cm^2$ metal at 5% $CO_2$ and 37° C. for 72 hours, periodically shaken to prevent localization of degradation products in solution around the sample. After 72 hours, the media containing the degradation products was supplemented with 10% FBS and used for subsequent cell culture toxicity studies. 7F2 mouse osteoblast cells, seeded onto TCPS at a density of 6000 cells/$cm^2$, were cultured for 3 days in complete media containing the degradation products at varying concentrations of 100, 50, 10, and 0. After 3 days, the culture medium was collected and assayed for LDH content and the cells were lysed for picogreen DNA quantification. 7F2 cells cultured on TCPS with Triton X-100 supplemented to media for a total concentration of 1% for 45 minutes serves as a high toxicity control while cells cultured without Triton X-100 serves as a low toxicity control.

Morphology

7F2 mouse osteoblasts cultured on oxidized alloy samples for up to 6 days were fixed in 2% glutaraldehyde (Fisher Scientific, Pittsburgh, Pa.) for 30 minutes. Samples were then dehydrated in 30%, 50%, 70%, and 100% ethanol for 5 minutes each. Fixed samples were then frozen and lyophilized overnight prior to carbon coating SEM (FEI XL40, Angstrom Scientific, Ramsey, N.J.).

Statistical Analysis

Statistical analysis was performed with Graphpad Instat 3.1. The differences between different groups were analyzed using single factor ANOVA followed by a Tukey-Kramer test.

Microstructural Characterization and Mechanical Properties

Chemical analysis of the metal alloy indicates the nominal composition to be Mg-2.8Sc-3.0Y, which is close to the targeted composition. The microstructure of the metal alloy comprised fine equiaxed grains with an average size of 109 μm, as shown in FIG. 1. The grain size is more than 8 times smaller than binary Mg-3Y under similar conditions. The reduction in grain size is beneficial for Mg alloys, as it is known to reduce degradation rate and increase strength.

Figure 2:
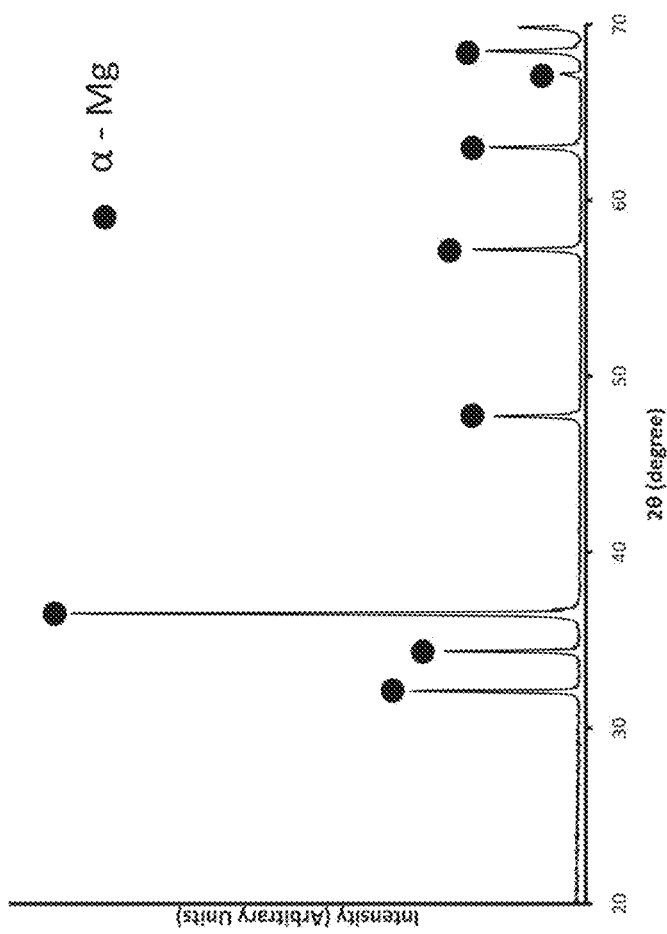
FIG. 2 is an xray diffraction plot showing Mg-3Sc-3Y alloy homogenized at 500° C. for 8 hours. It confirms that the metal alloy is in complete solid solution with the only peaks being identified belonging to α-Mg.
Figure 3:
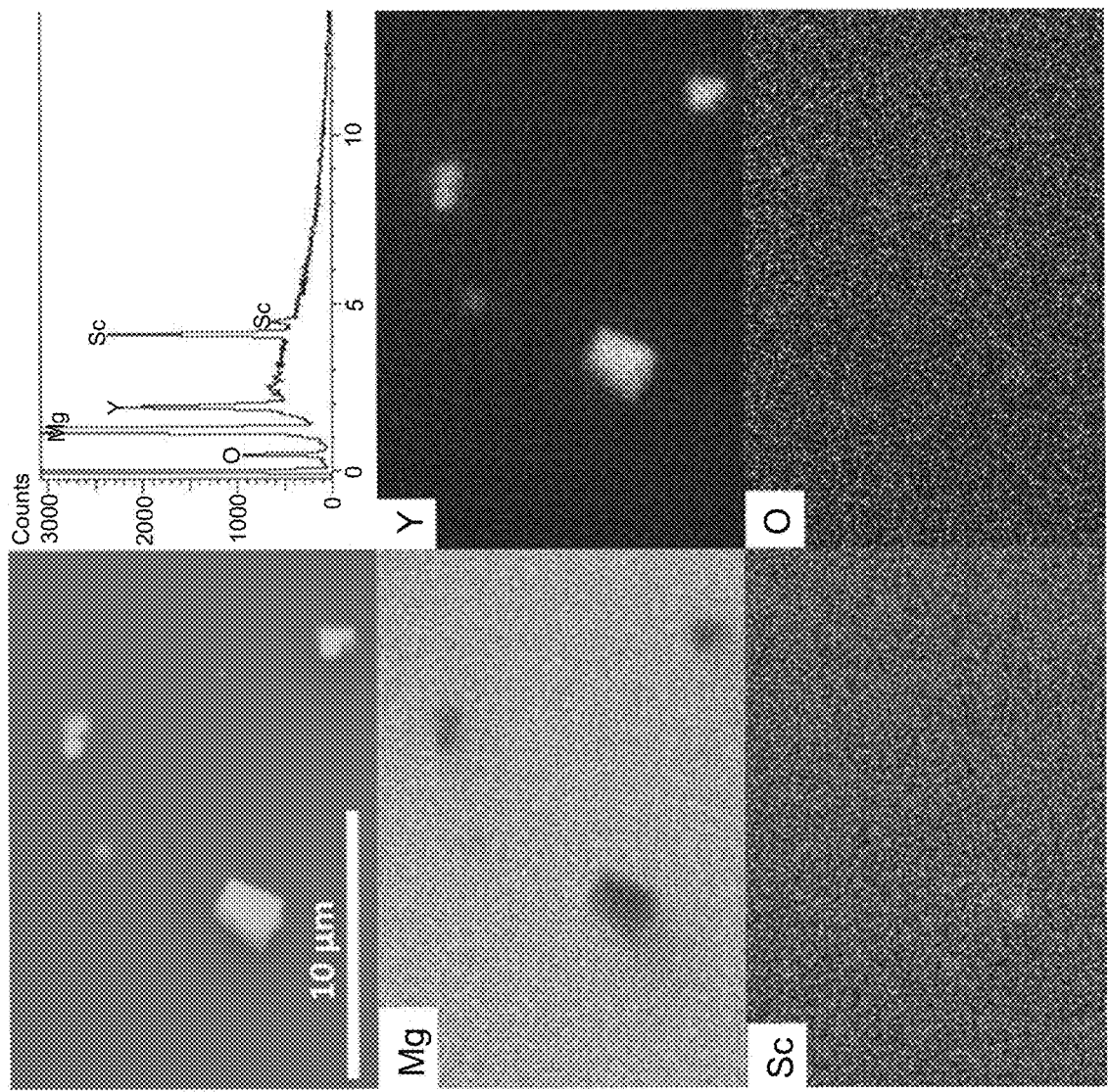
FIG. 3 depicts elemental maps for O, Mg, Sc and Y showing the presence of Y rich precipitates in solution treated Mg-3Sc-3Y alloy.

The XRD analysis of the alloy is shown in FIG. 2 and confirms that the alloy is in complete solid solution with the only peaks being identified belonging to α-Mg only, and no secondary phases were found. Subsequent SEM analysis of the microstructure did reveal the precipitation of a secondary phase in the microstructure. Due to the low volume fraction of particles present, detection of this phase was outside the limits of the XRD. To identify the constituents of this phase, EDS analysis was performed on the samples. FIG. 3 shows the SEM image of the microstructure with the elemental maps for Mg, O, Y, and Sc. It can be seen that the second phase particles present are a Y-rich binary phase. Based on the elemental analysis, binary phase diagram and the morphology of the particles, the second phase was identified as $Mg_{24}Y_5$ phase particles. These particles are not expected to be thermodynamically stable as the alloy composition lies in a single-phase region at 500° C. on the phase diagram. However, in alloys containing more that 3 wt % Y, small amount of Y-rich secondary phases have been previously reported even after solution treatment. It is believed that these particles precipitate due to the non-equilibrium solidification of the alloys, and do not completely dissolve during solution treatment due to their slow dissolution kinetics. It can also be seen that Sc is evenly distributed throughout the matrix and no detectable Sc rich secondary phase is present.

Addition of Sc and Y improved the mechanical properties of pure Mg primarily due to solid solution strengthening, grain size reduction, and a small amount of precipitation strengthening. The measured value of Vickers hardness of the alloy was 48.5±3.9 HV. The compressive yield strength of the alloys was found to be 100±3.5 MPa and the ultimate compressive strength was 357±12 MPa, which is comparable to the ultimate compressive strength of other cast alloys such as AZ91 and WE43. Since the alloy microstructure predominantly consists of solid solution, artificial aging treatment can be used to further increase its strength by precipitation strengthening.

Oxidation Behavior

Figure 4:
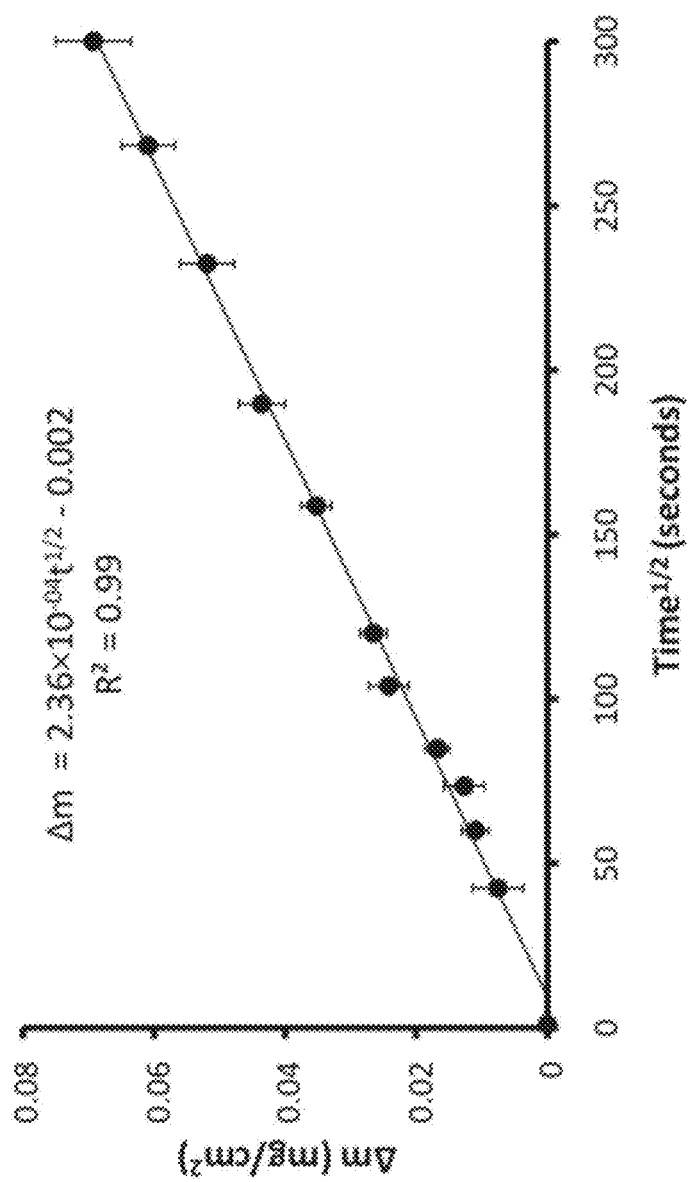
FIG. 4 is a graph depicting the weight gain per unit area versus the square root of time during oxidation of Mg-3Sc-3Y alloy.

The thermo-gravimetric analysis showed the parabolic nature of the oxidation behavior, with a higher rate of oxidation associated with the initial adsorption of oxygen and initial scale formation, followed by slow oxide growth. This behavior of the oxide growth as a function of time growth can be fitted to the parabolic equation (2) as:

$$\Delta m = (k_p t)^{1/2} + c \qquad (2)$$

where $\Delta m$ is the weight gain per unit area, $k_p$ is the parabolic rate constant, t is the oxidation time and c is a constant. The linear fit between the $\Delta m$ and $time^{1/2}$ was used to calculate the rate constant and is shown in FIG. 4. The calculated rate constant for Mg-3 Sc-3Y at 500° C. is $5.57 \times 10^{-8}$ $mg/cm^2/s$. The oxidation rate constant is an order of a magnitude smaller than binary Mg-4.3Y alloy and two orders of magnitude smaller than Mg-10Gd-3Y alloys, showing that the addition of Sc leads to the formation of an improved protective oxide layer as compared to Y and Gd additions.

Figure 5:
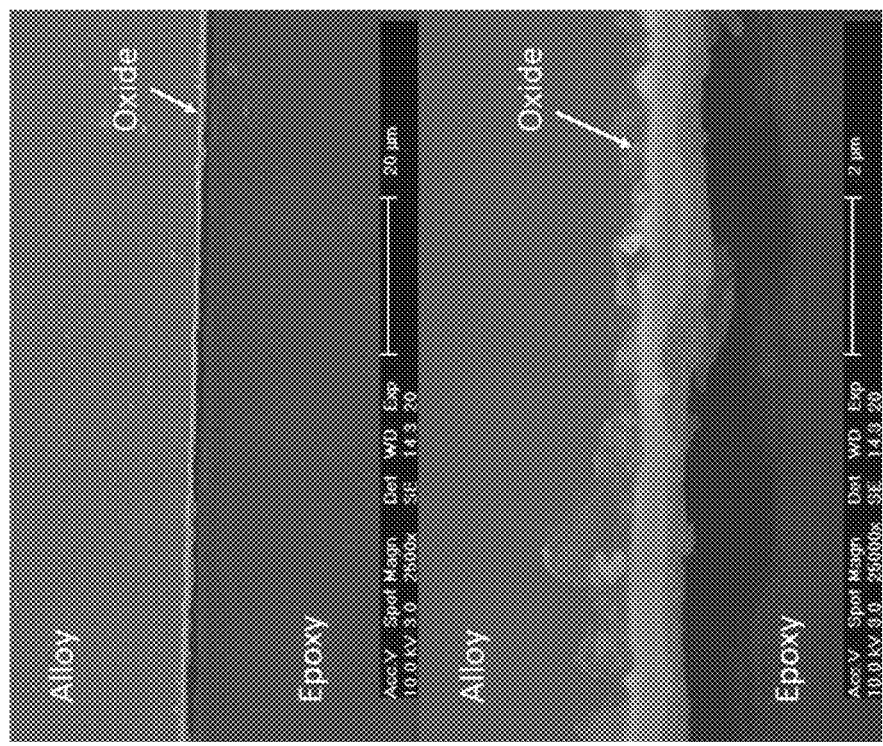
FIG. 5 depicts SEM images showing the cross section of Mg-3Sc-3Y alloy oxidized for 5 hours (a) low magnification (b) high magnification.
Figure 6:
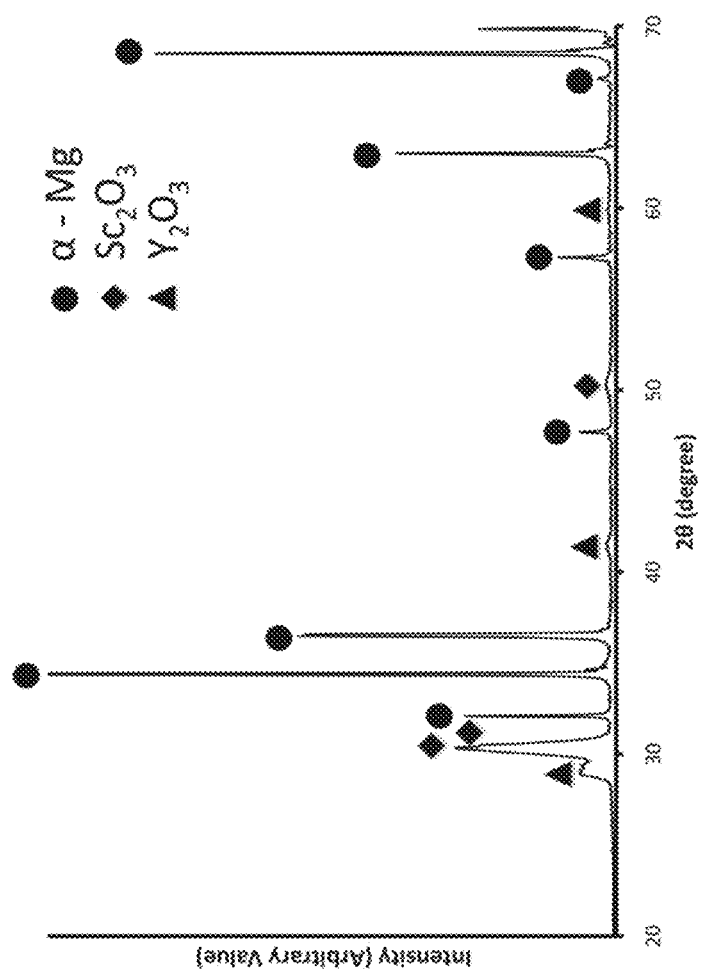
FIG. 6 is a xray diffraction plot showing the phases present in Mg-3Sc-3Y alloy oxidized 5 hours at 500° C.
Figure 7:
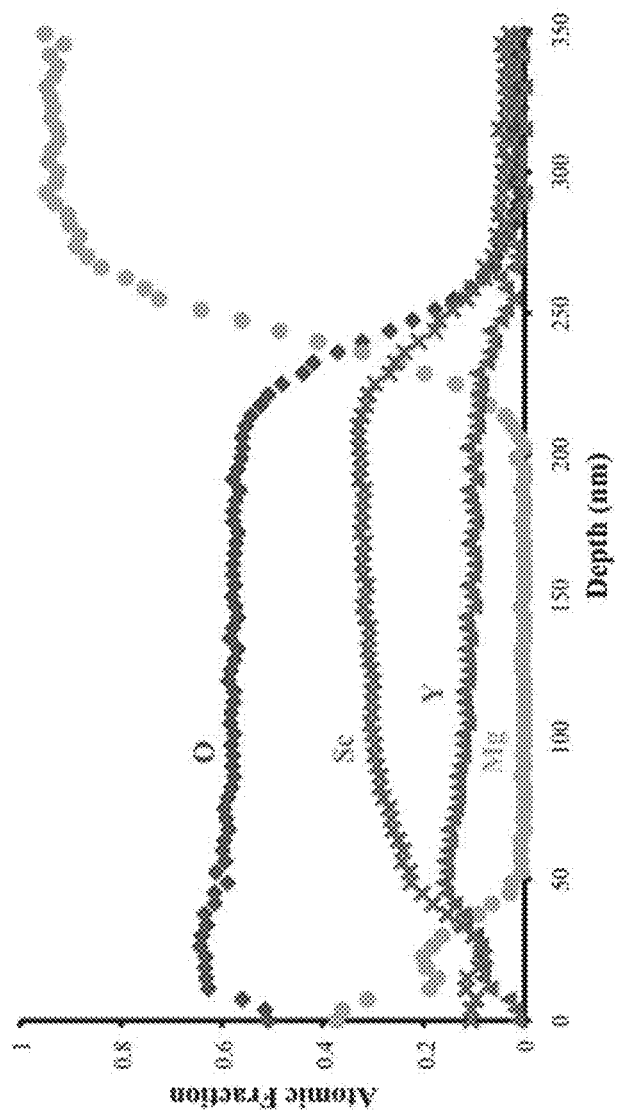
FIG. 7 is graph of depth profiling conducted using Auger electron spectroscopy; the graph shows that the upper layers comprise an oxide of scandium oxide and yttrium oxide, while the inner core comprises metallic magnesium, scandium and yttrium.

FIG. 5 shows the SEM images of the protective layer oxide cross-section where a thick and compact surface oxide can be seen. XRD analysis showed presence of both $Sc_2O_3$ and $Y_2O_3$, and is shown in FIG. 6. To further characterize the relative positions of binary oxides in the scale, Auger electron spectroscopy (AES) depth profiling was performed on the alloy and is shown in FIG. 7. It can be seen that the oxide depth profile consists of two different regions, with a thin outer Mg rich oxide layer and a thick inner Sc and Y oxide rich layer.

The composition of the protective layer was studied using xray diffraction, electron spectroscopy for chemical analysis, and Auger electron spectroscopy. The protective layer comprises scandium oxide and vanadium oxide in addition to magnesium oxide. The outermost layer comprises a larger amount of magnesium oxide and a smaller amount of scandium oxide, while the lower layer comprises a larger amount of scandium oxide and yttrium oxide than the magnesium oxide. The protective layer can therefore be a multilayered protective layer that is formed in-situ without the use of an external force field or an artificial force field. The multilayered protective layer is not formed by manual effort (or by an artificial effort) of coating one layer over the other.

FIGS. 6 and 7 are graphs that depict the composition of the metal oxide layer. FIG. 6 is a graph of xray diffraction of a metal alloy having a protective layer that comprises a metal oxide of scandium oxide and yttrium oxide. The magnesium oxide does not appear in this graph because of detection limits of the instrument being reached, i.e., the instrument is not capable of detecting magnesium oxide.

FIG. 7 is a graph of the surface protective layer. This graph was obtained by depth profiling of the protective layer conducted using Auger electron spectroscopy. From the graph, it may be seen that the first 1 to 50 nanometers of the protective layer comprise primarily magnesium oxide, with small amounts of scandium oxide and yttrium oxide. From about 50 nanometers to about 200 nanometers, the protective layer comprises both scandium oxide and yttrium oxide, with a very small amount of magnesium oxide. As can be seen in the FIG. 7, the (atomic fraction) amount of scandium oxide is greater than the amount of yttrium oxide. At a depth of about 250 nanometers, it can be seen that the protective layer no longer exists and the bulk of the metal alloy begins to be profiled.

Additionally, it can also be seen that Sc and Y are present throughout the depth of the oxide scale, with Sc concentration in the oxide being higher than Y concentration. This shows that the oxide layer has higher amount of $Sc_2O_3$ than $Y_2O_3$. This is primarily due to two reasons: 1) the matrix has higher Sc content in the solid solution as some of the Y was consumed in the formation of $Mg_{24}Y_5$ particles (FIGS. 1 and 2); and 2) as a first order approximation, since Sc has smaller atomic size as compared to Y it is anticipated to have a higher diffusion rate of Sc in Mg, and hence migrate to the surface faster.

Based on the overall analysis, the oxide consists of a thin outer region of a mixture of MgO, $Sc_2O_3$ and $Y_2O_3$ and a thicker inner region consisting only of $Sc_2O_3$ and $Y_2O_3$. This oxidation behavior can be explained by the thermodynamic parameters of the system. During oxidation, the following reactions can take place:

$$2Mg + O_2(g) \rightarrow 2MgO \qquad (3)$$

$$2Y + \frac{3}{2}O_2 \rightarrow Y_2O_3 \qquad (4)$$

$$2Sc + \frac{3}{2}O_2 \rightarrow Sc_2O_3 \qquad (5)$$

The Gibbs free energies ($\Delta G_f$) of these reactions at the oxidation temperature (500° C.) are −522.0, −1,682.8 and −1,675.4 kJ respectively. Additionally, since oxides with higher thermodynamic stability can reduce the oxides with lower stability, the following reactions can occur during the oxidation process:

$$2Y + 3MgO \rightarrow Y_2O_3 + 3Mg \qquad (6)$$

$$2Sc + 3MgO \rightarrow Sc_2O_3 + 3Mg \qquad (7)$$

Under the experimental conditions, Gibbs free energy ($\Delta G_t$) for the above reactions can be calculated using the following equation, $$\Delta G_T = \Delta G_T^0 + RT\ln\frac{a_{Mg}^3}{a_{RE}^2} \qquad (8)$$

where $\Delta G_T^0$ is the standard Gibbs free energy of the reaction at temperature T, $\alpha_{Mg}$ and $\alpha_{RE}$ are the activities of Mg and rare earth metals, respectively. For simplification, the activities of Mg, Sc and Y were replaced by their molar atomic concentrations. The activity of pure oxygen was used as one. Based on these the calculations, the $\Delta G_{500}$ values for reactions 6 and 7 are:

$$\Delta G_{500}^Y = -93.2 \text{ kJ} \qquad (9)$$

$$\Delta G_{500}^{Sc} = -89.2 \text{ kJ} \qquad (10)$$

The above calculations show that in presence of Sc and Y, MgO will be reduced to Mg and $Sc_2O_3$ and $Y_2O_3$ will form preferentially. Additionally, since the thermodynamic driving force for formation of Sc and Y are similar, these oxides are capable of existing simultaneously in the oxide scale, as shown by the AES analysis.

Degradation Rates and Profiles

Figure 8:
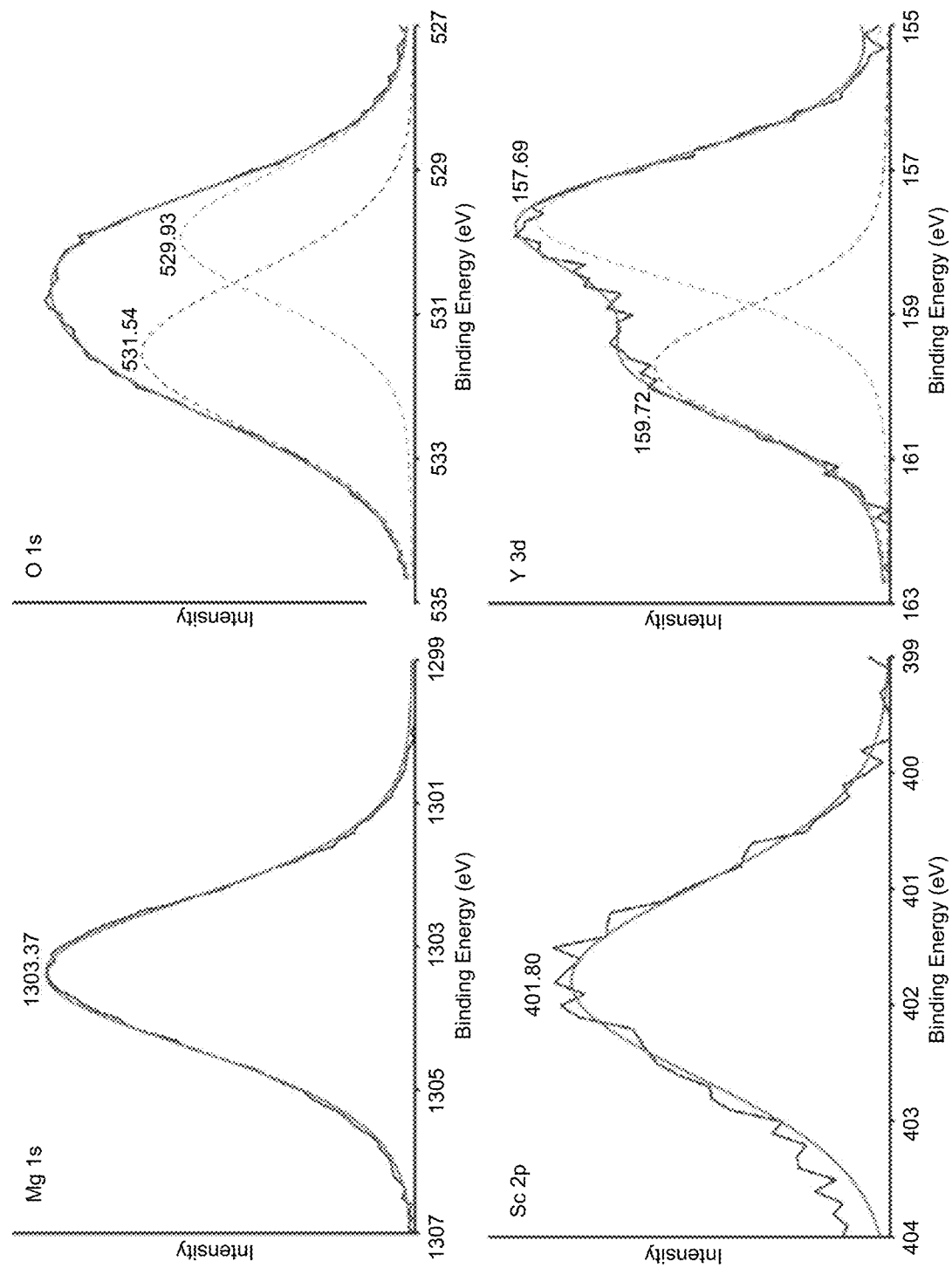
FIG. 8 depicts xray photoelectron spectra (XPS) multiplex peaks for Mg, O, Sc and Y, showing the presence of MgO, $Sc_2O_3$ and $Y_2O_3$ in the outermost layer of oxide scale.

The hydrogen evolution studies demonstrate that the presence of surface oxide reduces the degradation rate as can be seen in the FIG. 8. The hydrogen evolution rate of the polished alloy was approximately 1.1 ml/cm²/day, which is significantly lower than the rate of commercially pure Mg (26 ml/cm²/day) and alloys such as Mg-1Y and ZE41, and comparable to alloys Mg-1Ca-0.5Sr, Mg-1Zn and Mg-1Al. It is further observed that the oxidation of the alloy at 500° C. for 5 hours leads to the initial reduction in the degradation rate from 1.1 ml/cm²/day to 0.16 ml/cm²/day, which is lower than AZ91 and WE43 alloys. The oxide layer was able to remain protective and maintain the low degradation rate for 7 days, after which the degradation rate was increased to that of the polished sample. This shows that the oxide layer provides protection from the degradation and once the oxide layer is degraded, the degradation rate returns to that of the bulk material. It is anticipated that for practical medical applications, surface passivation may be desired for longer periods of time. This can be achieved by increasing the oxide thickness by oxidizing for longer time period. Therefore, samples oxidized for 24 hours were also analyzed to see the effect of oxide thickness on the degradation rate. As compared to the polished samples, the samples oxidized for 24 hours showed 100 fold reduction in the hydrogen evolution rate, reducing it to 0.01 ml/cm²/day for up to 23 days. Thus, changing the oxidation time proved to be an effective method for controlling the surface passivity of the alloy. This rate is lower than most of the commercially available Mg alloys and is comparable to that of high purity Mg. The relative reduction in degradation rate due to the oxide layer is comparable or better than that from MAO and other deposition coatings such as dicyclopentadiene and hydroxyapatite.

Cytotoxicity

Figure 9:
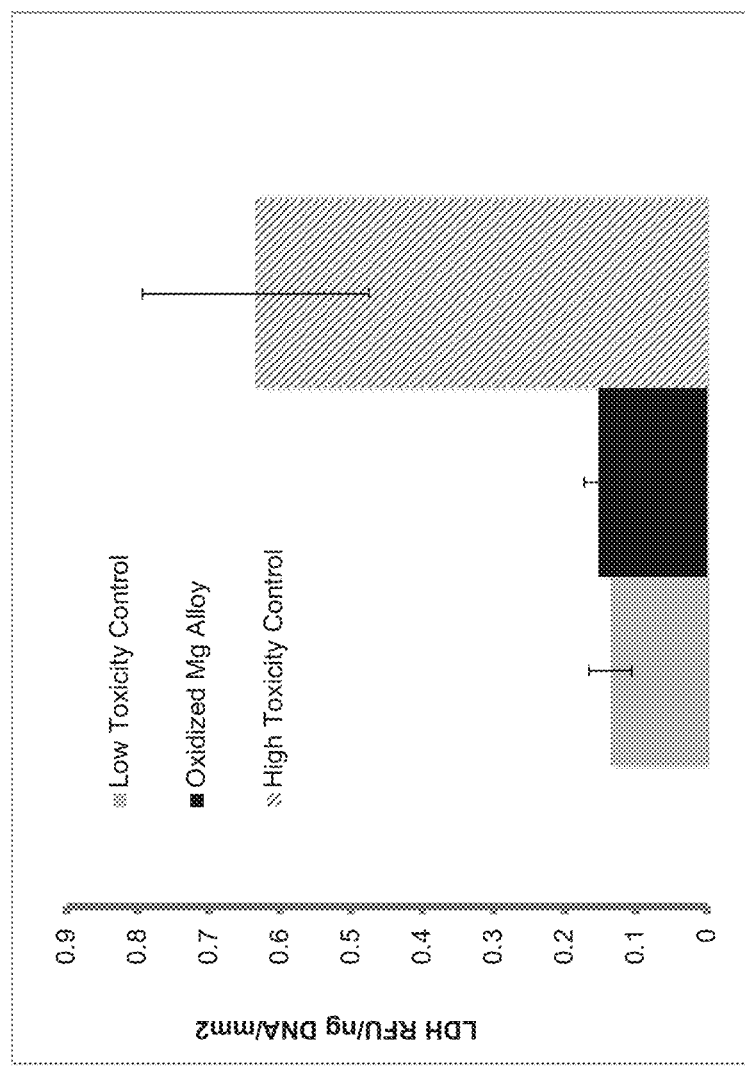
FIG. 9 is a bar graph that depicts cytotoxicity of 7F2 mouse osteoblast cells cultured on oxidized alloy (black bar) as compared to both high toxicity (striped bar) and low toxicity (grey bar) control cultures. Data are Mean±SD with n=3.

This study intended to determine the potential in vitro toxic effect of a novel alloy containing Sc and Y. Results depicted in FIG. 9 show the cytotoxicity of oxidized alloy to 7F2 mouse osteoblast cells after 6 days of culture. Relative to the high toxicity control that represents total cell cytotoxicity, and the low cytotoxicity control that represents baseline cell lysis in growth media, the cells cultured on the alloy exhibited 3% toxicity. These results are encouraging and demonstrate that the oxidized alloy does not exhibit significantly more cytotoxicity than cells grown on TCPS in complete media ($p<0.05$). Due to the limited toxicity information of Sc and Y available in literature, these preliminary toxicity studies were necessary before performing further testing of this materials biocompatibility. The ternary alloy and its oxide layer do not pose a significant risk of toxicity to cells in the early time points when initial cell attachment and proliferation is occurring. While Mg alloys have been studied for their biocompatibility, the passivating oxide layer presented here reduces the degradation rate of the material and these results show that this layer does not cause toxicity. This data shows that the initial in vitro response of 7F2 osteoblasts to the oxidized Mg alloy is that of low to no toxicity, with the percentage of cell death being similar to that of normal healthy cultures.

Toxicity of Degradation Products

Figure 10:
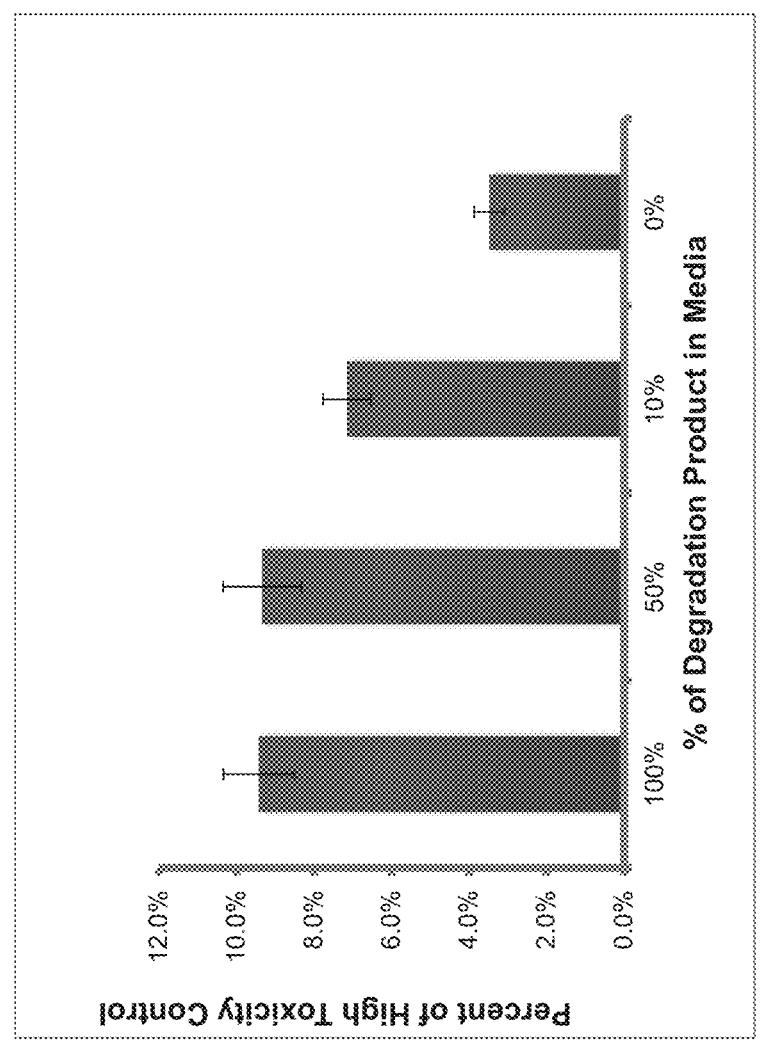
FIG. 10 is a bar graph that depicts the toxicity of 7F2 mouse osteoblast cells cultured in complete media supplemented with 100, 50, 10, and 0% of the unoxidized alloy degradation products after 72 hours of degradation. Data shown are quantified LDH from culture media relative to the high toxicity control. Data are Mean+/−SD with n=3.

The initial burst of degradation products as the material moves toward an equilibrium concentration with its environment is often a concern in biomedical applications. Similar to drug delivery systems, where the burst release of pharmaceutics can exceed toxic levels, a material releasing degradation products into solution can pose a threat to neighboring cells. Non-oxidized samples of Mg-3 Sc-3Y were tested to simulate the release of ions once the oxide scale has corroded and the degradation rate increases. FIG. 10 shows the toxicity of degradation products on 7F2 cells from non-oxidized Mg alloy degraded for 72 hours. Cells cultured in 100% degradation product showed a toxicity of 9% of the high toxicity control. This data shows that the ions present in solution after 72 hours of degradation do not cause significant ($p<0.05$) harm to cells exposed to the degrading alloy. Here, we show that the concentrations associated with the initial burst of ions are not toxic to the cells and do not cause significant cell lysis or cytotoxicity. When considering a material for in vivo applications, in addition to cytotoxic effects on cells attached to the material, it is essential to consider the effects of the degradation products on the surrounding tissue. Therefore, these data demonstrate that as the material degrades, beyond the oxide layer, the degradation products do not cause an initial toxic response from the cells. Although promising, these results warrant additional studies to observe other cell type interactions with the material as well as proliferation studies. An investigation into cellular proliferation would be important into the ability of this material to support proliferation and tissue growth. Additionally, long-term toxicity studies evaluating the effect of the material as it degrades entirely would provide additional insight into how the material would behave if implanted in a biomedical application. The preliminary data described here are promising and provide a foundation for future work to fully characterize the biocompatibility of this material.

In this study, degradation control of Mg based alloys by selective oxidation was investigated and the efficacy of Sc and Y as alloying additions in forming a self-passivating protective oxide was demonstrated. It was found that the oxide layer mainly consists of $Sc_2O_3$ and $Y_2O_3$, with higher amount of $Sc_2O_3$ than $Y_2O_3$. When compared to the polished surface, the oxide layer reduced the degradation rate by almost 100 times to 0.01 ml/cm$^2$/day for up to 23 days. The alloying additions also increased the compressive strength of the alloy, which was comparable to the strength of AZ91 and WE43 alloys. In-vitro cyto-compatibility analysis demonstrated cell attachment to the oxidized alloy surface. No significant toxicity was detected. Analysis of degradation products of non-oxidized alloys further proved the lack of toxicity of the effluents that are the by-products of the degradation process. This investigation confirms that selective oxidation through alloying with Sc and Y is an effective method to control the degradation rate of an implant material, especially in applications where the implant geometry restricts the ability to use coating technologies.

While this disclosure describes exemplary embodiments, it will be understood by those skilled in the art that various changes can be made and equivalents can be substituted for elements thereof without departing from the scope of the disclosed embodiments. In addition, many modifications can be made to adapt a particular situation or material to the teachings of this disclosure without departing from the essential scope thereof. Therefore, it is intended that this disclosure not be limited to the particular embodiment disclosed as the best mode contemplated for carrying out this disclosure.

What is claimed is:

1. A method comprising:
    blending three or more metals to form a metal alloy, where the metal alloy comprises a base metal, a second element and a third element; where the base metal is magnesium, calcium, strontium, zinc, or a combination thereof; where the second element is chemically different from the third element; and where the second element and the third element are scandium, yttrium, gadolium, cerium, neodymium, dysporium, or a combination thereof;
    molding the metal alloy; and
    annealing the metal alloy at a temperature and in an atmosphere effective to produce a protective layer on the metal alloy; where the protective layer is reactively bonded to the metal alloy and where the protective layer is non-metallic, where the protective layer comprises a base non-metallic derivative, a second non-metallic derivative and a third non-metallic derivative of metals present in the metal alloy; and where the base non-metallic derivative, the second non-metallic derivative and the third non-metallic derivative are all chemically different from one another.

2. The method of claim 1, where the metal alloy is annealed at a temperature of about 25 to about 800° C.

3. The method of claim 1, where the atmosphere contains oxygen, carbon, boron, silicon, selenium, fluorine, bromine, iodine, tellurium, sulfur, nitrogen, or a combination thereof.

4. The method of claim 1, where the metal alloy comprises a base metal, a second element and a third element; where the base metal is magnesium, calcium, strontium, zinc, or a combination thereof; where the second element is chemically different from the third element; and where the second element and the third element are scandium, gadolium, cerium, neodymium, dysporium, or a combination thereof; and
    where the protective layer comprises a base non-metallic derivative, a second non-metallic derivative and a third non-metallic derivative of metals present in the metal alloy; and where the base non-metallic derivative, the second non-metallic derivative and the third non-metallic derivative are all chemically different from one another.

5. The method of claim 4, where the protective layer comprises a plurality of layers; with an outermost layer comprising an oxide of magnesium, calcium, strontium, or a combination thereof; while an inner layer comprises an oxide of scandium, gadolium, cerium, neodymium, dysporium, or a combination thereof.

6. The method of claim 4, where the protective layer has a thickness of 0.1 nanometers to 500 nanometers.

7. The method of claim 4, wherein the base metal is magnesium.

8. The method of claim 4, wherein the base metal is calcium.

9. The method of claim 4, wherein the base metal is strontium.

10. The method of claim 4, wherein the base metal is zinc.

11. The method of claim 4, wherein the base metal is magnesium, the second element is scandium, and the third element is cerium.

12. The method of claim 1, where the metal alloy comprises a base metal, a second element and a third element; where the base metal is calcium, strontium, zinc, or a combination thereof where the second element is chemically different from the third element; and where the second element and the third element are scandium, yttrium, gadolium, cerium, neodymium, dysporium, or a combination thereof; and
    where the protective layer comprises a base non-metallic derivative, a second non-metallic derivative and a third non-metallic derivative of metals present in the metal alloy; and where the base non-metallic derivative, the second non-metallic derivative and the third non-metallic derivative are all chemically different from one another.

13. The method of claim 12, where the protective layer comprises a plurality of layers; with an outermost layer comprising an oxide of calcium, strontium, or a combination thereof; while an inner layer comprises an oxide of scandium, yttrium, gadolium, cerium, neodymium, dysporium, or a combination thereof.

14. The method of claim 12, wherein the second element is yttrium and the third element is scandium.

15. The method of claim 12, wherein the second element is yttrium and the third element is selected from gadolium, cerium, neodymium, dysporium, or a combination thereof.

16. The method of claim 12, wherein the second element is scandium and the third element is selected from gadolium, cerium, neodymium, dysporium, or a combination thereof.

17. The method of claim 1, where the metal alloy comprises a base metal, a second element and a third element; where the base metal is magnesium, calcium, strontium, zinc, or a combination thereof where the second element is chemically different from the third element; and where the second element and the third element are gadolium, cerium, neodymium, dysporium, or a combination thereof;
where the protective layer comprises a base non-metallic derivative, a second non-metallic derivative and a third non-metallic derivative of metals present in the metal alloy; and where the base non-metallic derivative, the second non-metallic derivative and the third non-metallic derivative are all chemically different from one another; and
wherein the protective layer comprises a plurality of layers; with an outermost layer comprising an oxide of magnesium, calcium, strontium, or a combination thereof while an inner layer comprises an oxide of gadolium, cerium, neodymium, dysporium, or a combination thereof.

18. The method of claim 17, wherein the outermost layer is an oxide of magnesium.

19. The method of claim 17, wherein the outermost layer is an oxide of calcium.

20. The method of claim 17, wherein the outermost layer is an oxide of strontium or an oxide of zinc.

* * * * *